United States Patent
Steinle et al.

(10) Patent No.: US 10,603,120 B2
(45) Date of Patent: Mar. 31, 2020

(54) OPTIMIZED SEMI-ROBOTIC ALIGNMENT WORKFLOW

(71) Applicant: Brainlab AG, Munich (DE)

(72) Inventors: Wolfgang Steinle, Munich (DE); Christian Rabus, Munich (DE); Nils Frielinghaus, Heimstetten (DE)

(73) Assignee: BRAINLAB AG, Munich (DE)

( * ) Notice: Subject to any disclaimer, the term of this patent is extended or adjusted under 35 U.S.C. 154(b) by 267 days.

(21) Appl. No.: 15/566,096

(22) PCT Filed: Sep. 13, 2016

(86) PCT No.: PCT/EP2016/071556
§ 371 (c)(1),
(2) Date: Oct. 12, 2017

(87) PCT Pub. No.: WO2018/050207
PCT Pub. Date: Mar. 22, 2018

(65) Prior Publication Data
US 2019/0046278 A1     Feb. 14, 2019

(51) Int. Cl.
*A61B 34/00*     (2016.01)
*A61B 34/20*     (2016.01)
(Continued)

(52) U.S. Cl.
CPC .............. *A61B 34/30* (2016.02); *A61B 34/10* (2016.02); *A61B 34/20* (2016.02); *A61B 34/25* (2016.02);
(Continued)

(58) Field of Classification Search
CPC ......... A61B 34/10; A61B 34/20; A61B 34/25; A61B 34/30; A61B 2034/107;
(Continued)

(56) References Cited

U.S. PATENT DOCUMENTS

| 8,660,635 B2 * | 2/2014 | Simon ................. G06F 19/3481 600/424 |
| 8,738,181 B2 | 5/2014 | Greer et al. |

(Continued)

OTHER PUBLICATIONS

International Search Report and Written Opinion for PCT/EP2016/071556 dated May 22, 2017.

*Primary Examiner* — Robert T Nguyen
(74) *Attorney, Agent, or Firm* — Middleton Reutlinger

(57) ABSTRACT

Disclosed is a medical data processing method for determining control data for an automated movement of a robotic system (1) to move a tool operatively associated with the robotic system (1), wherein the method comprises executing, on at least one processor of at least one computer (4), steps of: a) acquiring (S1) image data describing an image of an anatomical structure of a patient; b) determining (S2) planned position data, based on the image data, describing at least one planned position of the tool relative to the anatomical structure of the patient; c) acquiring (S3) status change data describing the change of data a status of the robotic system (1) from a first status to a second status, wherein in the first status a manual movement of at least one part of the robotic system (1) is allowed and in the second status a manual movement of the at least one part of the robotic system is inhibited; d) acquiring (S4) actual position data describing the actual position of an element of the statue change data robotic system, in particular the tool, relative to the anatomical structure; e) determining (S5), based on the planned position data and the status change data and the actual position data, control data describing instructions for controlling, in the second status of the robotic system (1), at least one actuator to move the tool.

15 Claims, 3 Drawing Sheets

(51) Int. Cl.
    *A61B 34/30*     (2016.01)
    *A61B 34/10*     (2016.01)
    *A61B 90/00*     (2016.01)
    *G16Z 99/00*     (2019.01)
    *G06F 19/00*     (2018.01)

(52) U.S. Cl.
    CPC ... *A61B 2034/105* (2016.02); *A61B 2034/107* (2016.02); *A61B 2034/2055* (2016.02); *A61B 2090/364* (2016.02); *G06F 19/00* (2013.01); *G16Z 99/00* (2019.02)

(58) Field of Classification Search
    CPC ...... A61B 2034/2055; A61B 2034/105; A61B 2090/364; G16Z 99/00; G06F 19/00
    See application file for complete search history.

(56) References Cited

U.S. PATENT DOCUMENTS

| | | | |
|---|---|---|---|
| 2009/0259230 A1 | 10/2009 | Khadem et al. | |
| 2013/0172905 A1* | 7/2013 | Iorgulescu | A61B 17/17 606/130 |
| 2015/0196365 A1* | 7/2015 | Kostrzewski | A61B 17/3417 606/130 |
| 2015/0036662 A1 | 12/2015 | Kostrzewski et al. | |
| 2015/0366624 A1 | 12/2015 | Kostrzewski et al. | |
| 2016/0081754 A1 | 3/2016 | Kostrzewski et al. | |
| 2017/0014998 A1* | 1/2017 | Langenfeld | B25J 9/1638 |
| 2019/0060007 A1* | 2/2019 | Fossez | A61B 34/20 |

\* cited by examiner

OPTIMIZED SEMI-ROBOTIC ALIGNMENT WORKFLOW

The present invention relates to a medical data processing method for an automated movement of a robotic system, a corresponding computer program, a non-transitory program storage medium storing such a program and a computer for executing the program, as well as a robotic system configured to control movement of a tool operatively associated with the robotic system.

TECHNICAL BACKGROUND

Robotic systems (including semi-robotic systems) are widespread in the medical field. In particular, robotic systems may be used for precise positioning of medical (e.g. surgical) tools. One way to move the tool to a target position is to perform a manual coarse-adjustment of a holding arm of the robotic system followed by an automated movement performed for example by a fine-adjustment unit.

In order to be safe enough regarding fault scenarios in risk analysis, the movement of the fine-adjustment unit may by authorized by actuating a physical switch, for example by pressing or holding a button arranged at the holding arm. However, actuating such a physical switch may interrupt the surgical workflow. If the switch was located close to a tool held by the holding arm, actuating the switch might alter the position of the tool. If the switch was located at the end of the holding arm opposite to the tool, draping might obstruct the switch.

The present invention allows for an improved alignment of a robotic system. In particular, the burden on a user (surgeon) for safely adjusting the robotic system is reduced.

Aspects of the present invention, examples and exemplary steps and their embodiments are disclosed in the following. Different exemplary features of the invention can be combined in accordance with the invention wherever technically expedient and feasible.

Exemplary Short Description of the Present Invention

In the following, a short description of the specific features of the present invention is given which shall not be understood to limit the invention only to the features or a combination of the features described in this section.

The disclosed method encompasses determining control data describing instructions for controlling automated movement of a robotic system to move a tool operatively associated with the robotic system. Determining the control data involves determining at least one planned position of the tool. Furthermore, a status change of the robotic system from a first status associated with a manual coarse-adjustment to a second status associated with an automated fine-adjustment as well as an actual position of an element of the robotic system, in particular the tool, are considered for determining the control data.

General Description of the Present Invention

In this section, a description of the general features of the present invention is given for example by referring to possible embodiments of the invention.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The disclosed method provides, in a first aspect, a medical data processing method for determining control data for an automated movement of a robotic system to move a tool operatively associated with the robotic system. The method comprises executing, on at least one processor of at least one computer, the following exemplary steps which are executed by the at least one processor.

In a (for example first) exemplary step, image data is acquired which describes (for example, defines) an image of an anatomical structure of a patient (for example, at least part of at patient's head). The patient image data may have been generated before the disclosed method is executed by applying a tomographic imaging modality (for example, a computed x-ray modality or a magnetic resonance imaging modality) to the anatomical structure of the patient. Alternatively, generation of the patient image data may be implemented as a step of the disclosed method.

In a (for example second) exemplary step, planned position data which describes (for example, defines) at least one planned position (for example, location and/or orientation) of the tool relative to the anatomical structure of the patient is determined. Determining the planned position data is based on the image data. In one example, the planned position is associated with (for example, defined by) a trajectory (also referred to as a target trajectory) comprising an entry point and a target point of the tool relative to the anatomical structure of the patient. The entry point and the target point may be selected manually by a surgeon, for example by selecting (for example, marking) the respective points on the image. The target point may be associated with a position of a region of interest (for example, a tumor). The entry point may be selected such that the target trajectory does not intersect with a specific part of the anatomical structure (for example, a critical structure). In one example, the entry point and the target point may be determined (for example, calculated) automatically. The planned position data may describe a plurality of planned positions (for example, a plurality of target trajectories) relative to the anatomical structure of the patient.

In a (for example third) exemplary step, status change data describing (for example, defining) the change of a status of the robotic system from a first status to a second status is acquired. In the first status a manual movement (for example, adjustment) of at least one part of the robotic system is allowed. In particular, in the first status a coarse-adjustment of at least one part of the robotic system is allowed. The manual movement (for example, adjustment) may be executed by a user (for example, a surgeon). In the second status a manual movement of the at least one part of the robotic system is inhibited. The first status of the robotic system may be associated with a coarse-adjustment mode of the robotic system. The second status of the robotic system may be associated with a fine-adjustment mode of the robotic system.

In one example, the robotic system comprises at least one holding arm and at least one robotic fine-adjustment unit. In particular, the robotic fine-adjustment unit is (for example, removably) attached to the holding arm. The tool (for example, a medical tool, in particular a surgical tool) operatively associated with the robotic system may be held by or may be integral with the robotic system. In one example, the tool may be comprised in the robotic system (for example, the tool may be a part, in particular an element, of the robotic system). In particular, the tool may be held by or may be integral with the robotic fine-adjustment unit.

In one embodiment, the holding arm may comprise at least one joint (for example, a hinge) and a locking mechanism (for example, a brake) associated with the joint. In the first status of the robotic system a manual movement of the holding arm may be allowed. In particular, a part of the holding arm may be manually moved (for example, adjusted) by movement of the joint for a coarse-adjustment of the robotic system. In the first status of the robotic system the locking mechanism associated with the joint may be in an unlocked status (also referred to as unlocked status of the holding arm), in which a manual movement of the holding arm is allowed. In the second status of the robotic system the locking mechanism associated with the joint may be in a locked status (also referred to as locked status of the holding arm), in which a manual movement of the holding arm is inhibited. In particular, the first status of the robotic system corresponds to (for example, is) the unlocked status of the holding arm, in which a manual movement of the holding arm is allowed, and the second status of the robotic system corresponds to (for example, is) the locked status of the holding arm, in which a manual movement of the holding arm is inhibited.

In one embodiment, a change of the status of the robotic system may be realized by means of at least one physical switch of the holding arm, for example a switch associated with the locking mechanism associated with the at least one joint of the holding arm. In particular, switching of the at least one physical switch changes the status of the robotic system. The status of the robotic system may be changed immediately after switching of the physical switch or after a predetermined period of time. In particular, the activation of a physical switch for a change of the status of the robotic system is less problematic than activating an authorization switch during a fine-adjustment of the robotic system.

In one example, a change of the status of the robotic system may be initiated manually, for example by touching or not touching a specific part (for example, a touch sensor) of the robotic system, in particular a specific part of the holding arm. In particular, if a specific part of the robotic system is touched, the at least one physical switch is switched and the locking mechanism associated with the joint changes from the locked status to the unlocked status (the robotic system changes from the second status to the first status). As soon as the specific part is not touched any more (for example, when the user removes his hand from the specific part) the physical switch is switched and the locking mechanism changes from the unlocked to the locked status (the robotic system changes from the first status to the second status).

Therefore, the status of the robotic system may be changed automatically from the first status to the second status, after a coarse-adjustment is finished. In particular, a change of the status (for example, a change from the unlocked status of the holding arm to the locked status of the holding arm) is detected by the robotic system and status change data is generated.

In one embodiment, the robotic fine-adjustment unit may comprise at least one actuator (for example, an electric motor). In one example, the robotic fine-adjustment unit comprises a plurality of actuators, in particular four or more than four actuators.

By controlling the at least one actuator the tool may be moved linearly. In one example, the tool may be moved along a trajectory (for example, a curved trajectory) by controlling the at least one actuator.

In a (for example fourth) exemplary step, actual position data describing the actual position (for example, location and/or orientation) of an element of the robotic system relative to the anatomical structure is acquired. In one example, the actual position of the element (for example the tool) of the robotic system is acquired by means of a tracking system, in particular an optical tracking system. In one example, the actual position of the element of the robotic system is acquired by determining the position of one or more joints of the robotic system.

The element of the robotic system for which the actual position is determined may be the tool operatively associated with the robotic system. Accordingly, the actual position data may directly describe the actual position of the tool. The element of the robotic system for which the actual position is determined may be an element (for example, a holding device for the tool) whose position relative to the tool is known. Accordingly, the actual position of the tool associated with the robotic system may be determined based on actual position data describing the actual position of the element of the robotic system.

In one example, the actual position of the element of the robotic system is associated with (for example, defined by) a trajectory (also referred to as actual position trajectory) describing an extension of the element. In particular, the actual position trajectory comprises information about the orientation of the element of the robotic system (for example, the tool or the holding device for the tool).

In a (for example fifth) exemplary step, control data describing instructions for controlling, in the second status of the robotic system, at least one actuator (for example, the at least one actuator comprised in the fine-adjustment unit) is determined. The control data is determined based on the planned position data, the status change data and the actual position data. In particular, the control data describes instructions for controlling the at least one actuator to move the tool from an actual position to a planned position. In one example, the actual position of the tool is described (for example, defined) by the actual position data and the planned position of the tool is described (for example, defined) by the planned position data.

In one embodiment, the control data is generated when the status of the robotic system changes from the first status to the second status (described by the status change data). In another embodiment, the control data is generated after a predetermined period of time after the status of the robotic system changes from the first status to the second status (described by the status change data).

In one example, determining the control data comprises selecting a planned position of the tool out of a plurality of planned position (described by the planned position data) based on a proximity to an actual position of the element (for example, the tool) of the robotic system (described by the actual position data). In particular, determining the control data comprises calculating a distance between the actual position of the element of the robotic system and the at least one planned position of the tool. In one example, determining the control data comprises calculating a distance between the actual position of the element of the robotic system and each planned position of the tool out of a plurality of planned positions of the tool (described by the planned position data).

In one embodiment, determining the control data comprises selecting a target trajectory out of a plurality of target trajectories described by the planned position data based on a proximity to an actual position of the element of the robotic system described by the actual position data. For example, by calculating the distance between a point associated with the actual position of the element of the robotic system and each target trajectory out of a plurality of target trajectories the closest trajectory may be determined. In particular, determining the control data comprises determining the target trajectory being closest to an actual position of the element of the robotic system (described by the actual position data) out of a plurality of target trajectories (described by the planned position data). The distance between the actual position of the element of the robotic system and a target trajectory may be calculated by determining the distance between a point (for example, the center point of the tool) associated with the actual position of the element of the robotic system and a point on the target trajectory (for example, the entry point or the target point).

The distance between the point associated with the actual position to a target trajectory may be calculated via determining the distance of the point to the orthogonal projection onto the target trajectory by means of the dot product.

In one example, selecting a target trajectory out of a plurality of target trajectories comprises determining an angle between the actual position trajectory and each target trajectory. The angle may be calculated from the arccosine of the dot product of the direction vectors. Selecting a target trajectory out of the plurality of target trajectories may comprise calculating a weighted average of the distances between the point associated with the actual position (for example, comprised in the actual position trajectory) of the element of the robotic system and each target trajectory and the respective angles between the actual position trajectory and each target trajectory. This way the most suitable target trajectory may be selected. Considering angles between the actual position trajectory and each target trajectory for selecting a target trajectory avoids selecting an unsuitable trajectory.

In one example, when (or after) the status of the robotic system is changed from the first status (for example, unlocked status of the holding arm) to the second status (for example, locked status of the holding arm) control data is generated to instruct the at least one actuator (for example, the at least one actuator comprised in the robotic fine-adjustment unit) to move the tool to a planned position (for example, a selected target trajectory). In one example, determining the control data comprises evaluating whether the tool can arrive at a planned position (for example, a selected target trajectory) by movement of the actuator. This may be determined by applying the inverse kinematics of the actuator (for example, the actuator comprised in the robotic fine-adjustment unit). In case of a linear movement of the actuator, the linear translation of the actuator may be determined. For more complex movements of the actuator numerical optimization methods for non-linear systems, for example the Jacobian Inverse technique may be applied. If the tool can arrive at the planned position, the actuator may be instructed to move. If the tool cannot arrive at the planned position, new (for example, updated) control data may be determined (for example, comprising selection of another target trajectory).

In one embodiment, the movement of the tool may me restricted by at least one constraint (for example a threshold value, in particular associated with a distance or time). In particular, the control data is associated with information describing a minimum distance between the tool and a part (for example a surface) of the anatomical structure of the patient. In particular, a plurality of points (for example, points arranged equidistantly) may be selected on the target trajectory. For each of these points a minimum distance to the part of the anatomical structure of the patient may be determined. If the movement of the tool cannot comply with the minimum distance, new (for example, updated) control data may be determined. This way an unwanted collision of the tool with the anatomical structure of the patient may be avoided.

In one example, the control data is associated with information describing a maximum time for moving the tool (for example, in the second status of the robotic system). In particular, the movement of the tool may be stopped, if a specific time constraint (for example, a predetermined time period describing a maximum time) has expired. After stopping the movement new (for example, updated) control data may be determined (for example, comprising selection of another target trajectory).

In one embodiment, the control data is associated with information describing an accuracy of movement of the robotic system. The information describing an accuracy of movement may comprise information regarding a predetermined maximal distance between the actual position of the element of the robotic system (for example, the actual position trajectory) and a point associated with the target trajectory (for example, the target point or the entry point) after performing a movement of the tool in the second status of the robotic system. In particular, determining the control data may comprise determining the distance between the actual position of the element of the robotic system (for example, the actual position trajectory) and a point associated with the target trajectory (for example, the target point or the entry point) after performing a movement of the tool in the second status of the robotic system. In particular the predetermined maximal distance is compared with the determined distance. If the determined distance is larger than the predetermined maximal distance, new (for example, updated) control data may be determined. Accordingly, movement of the tool may be continued until the planned position is reached with a desired accuracy.

In one example, the method comprises a step of outputting movement information data which describes if a movement of the tool in the second status of the robotic system is (currently) carried out or stopped. The movement information data may be used to generate information (for example, visual or acoustical information) about an undergoing or stopped movement of the tool in the second status of the robotic system. In particular, the robotic system may indicate if a movement of the tool in the second status is (currently) carried out or stopped.

In one embodiment, the control data comprises instructions for controlling the at least one actuator (for example, the at least one actuator comprised in the fine-adjustment unit) to a predetermined position, when the status of the robotic system changes from the second status (for example, locked status of the holding arm) to the first status (for example unlocked status of the holding arm). In particular, the predetermined position is a center position. The center position may particularly suitable for moving the tool to a planned position, when the status of the robotic system changes back to the second status. Accordingly, alignment of the tool in the second status of the robotic system may be improved by reducing the moving distance or the moving time of the tool.

In one example, the method comprises executing, on the at least one processor of the at least one computer, an exemplary step of acquiring atlas data describing an image-based model of the anatomical structure. Determining the planned position data may be further based on the atlas data, for example by comparing, specifically matching, the atlas data (the image-based model) to the image data. In particular, the comparing is done for example by applying an image fusion algorithm to the patient image data and the atlas data. Accordingly the burden on the user (for example, a surgeon) with regard to identifying a specific part of the anatomical structure is reduced. Therefore, planning the position of the tool is simplified.

When performing the claimed method no physical interaction with a navigation screen is necessary for aligning the instrument with planned positions (for example, target trajectories). Moreover, no manual actuation of an authorization switch is necessary for authorizing movement of the tool by the at least one actuator of the fine adjustment unit. The complexity of the system and the respective costs are reduced. An undesirable user interaction via additional foot or hand switches is avoided. The processing method may be performed by one user interacting with the holding arm (for coarse-adjustment) only, without having to leave the surgical workplace or having actions to be performed by other personnel or having to use additional devices.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect and/or to a (physical, for example electrical, for example technically generated) signal wave, for example a digital signal wave, carrying information which represents the program, for example the aforementioned program, which for example comprises code means which are adapted to perform any or all of the method steps described herein.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the at least one processor or is loaded into the at least one memory, or wherein the at least one computer comprises the program storage medium according to the third aspect.

In a fifth aspect, the invention is directed to a robotic system (for example, a semi-robotic system) configured to control an automated movement of a tool operatively associated with the robotic system, the robotic system comprising:

a) at least one holding arm;
b) at least one robotic fine-adjustment unit comprising at least one actuator,
c) the at least one computer according to the fourth aspect.

The at least one computer is operably associated with the at least one actuator.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web).

For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface.

The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium.

The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument).

For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder facing the marker and assists in placing the marker device on the marker holder in a force fit and/or positive fit.

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

A navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information.

Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Determining the position is referred to as referencing if it implies informing a navigation system of said position in a reference system of the navigation system.

The n-dimensional image of a body is registered when the spatial location of each point of an actual object within a space, for example a body part in an operating theatre, is assigned an image data point of an image (CT, MR, etc.) stored in a navigation system.

Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises positional information which can be matched (for example by applying an elastic or rigid image fusion algorithm) for example to positional information contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc.

Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

DESCRIPTION OF THE FIGURES

In the following, the invention is described with reference to the appended figures which represent a specific embodiment of the invention. The scope of the invention is however not limited to the specific features disclosed in the context of the figures, wherein

FIG. 1 is a flow diagram illustrating the basic steps of the disclosed method which in the illustrative example of FIG. 1 starts with a step S1 of acquiring image data. Then, step S2 is executed which encompasses determining planned position data. In subsequent step S3 status change data is acquired. In step S4 actual position data is determined. The last step shown in FIG. 1 is step S5 which is directed to determining control data.

FIG. 2 shows an exemplary robotic system 1 (for example, a semi-robotic system) for performing the disclosed method. The robotic system 1 comprises a holding arm 2, a robotic fine-adjustment unit 3 and a computer 4. Furthermore, FIG. 2 depicts a patient couch 5 (on which a patient is positioned) and a tracking system 4 (for example, comprised in a surgical navigation system).

Figure 1:
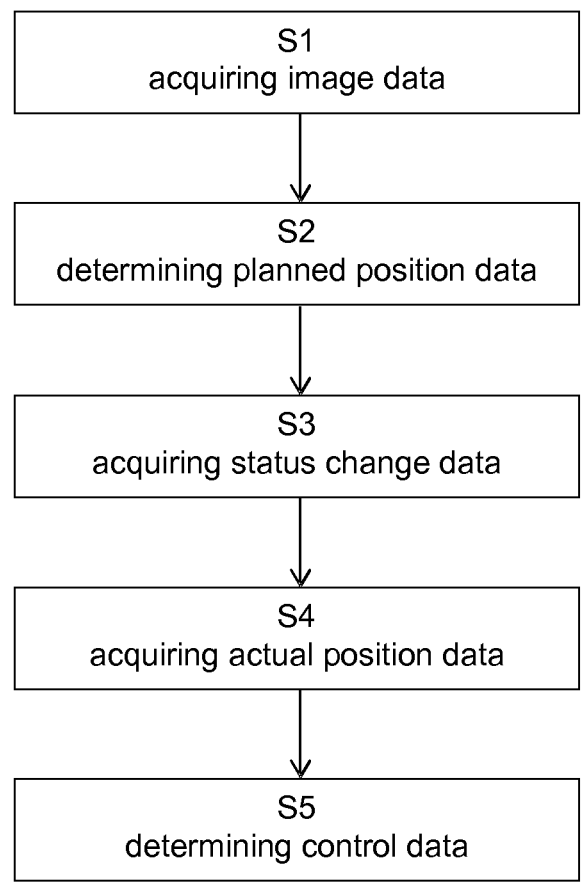
FIG. 1 is a flow diagram showing the basic steps of the disclosed method.

The holding arm 2 (for example, attached to the patient couch 5) comprises a plurality of joints and a locking mechanism (for example, a brake) associated with each joint. In a first status of the robotic system 1 (for example, an unlocked status of the holding arm 2) a manual movement of the holding arm 2 is allowed (for example, for a coarse-adjustment of the robotic system 1). In a second status of the robotic system 1 (for example, a locked status of the holding arm 2) a manual movement of the holding arm 2 is inhibited (for example, for a fine-adjustment of the robotic system 1 by the fine-adjustment unit 3).

The fine-adjustment unit 3 is (for example, removably) attached to the holding arm 2. The fine-adjustment unit 3 comprises at least one actuator to move a tool (for example, a surgical tool) held by the fine-adjustment unit 3.

The computer 4 is operatively associated with the at least one actuator of the fine-adjustment unit 3. The computer comprises at least one processor on which the control data describing instructions for controlling the actuator of the fine-adjustment unit 4 are determined. Moreover, the computer 4 is operatively associated with a display 8 showing a plurality of planned trajectories 9 (described by the planned position data).

Figure 2:
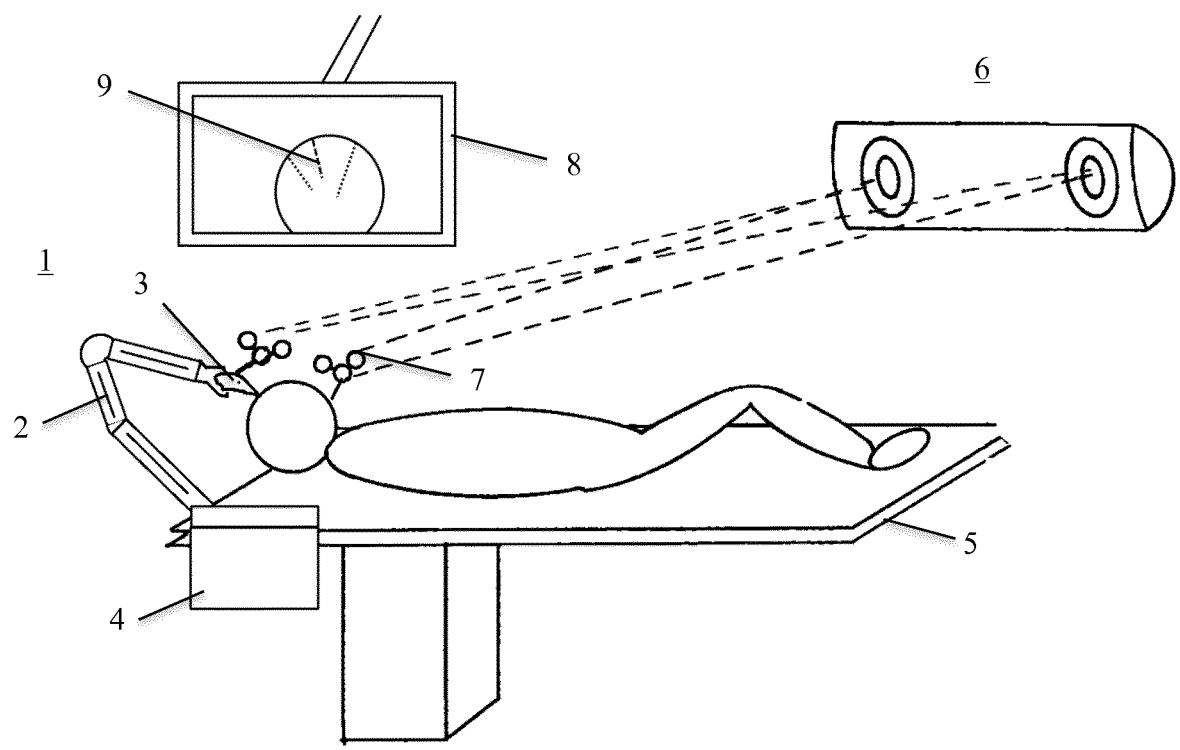
FIG. 2 shows an exemplary robotic system for performing the disclosed method.

The tracking system 6 is for example an optical tracking system, configured to detect marker devices 7 (for example, reference stars). As shown in FIG. 2, one marker device 7 is attached to the patient as a reference and one marker device 7 is attached to the fine-adjustment unit 3.

Figure 3:
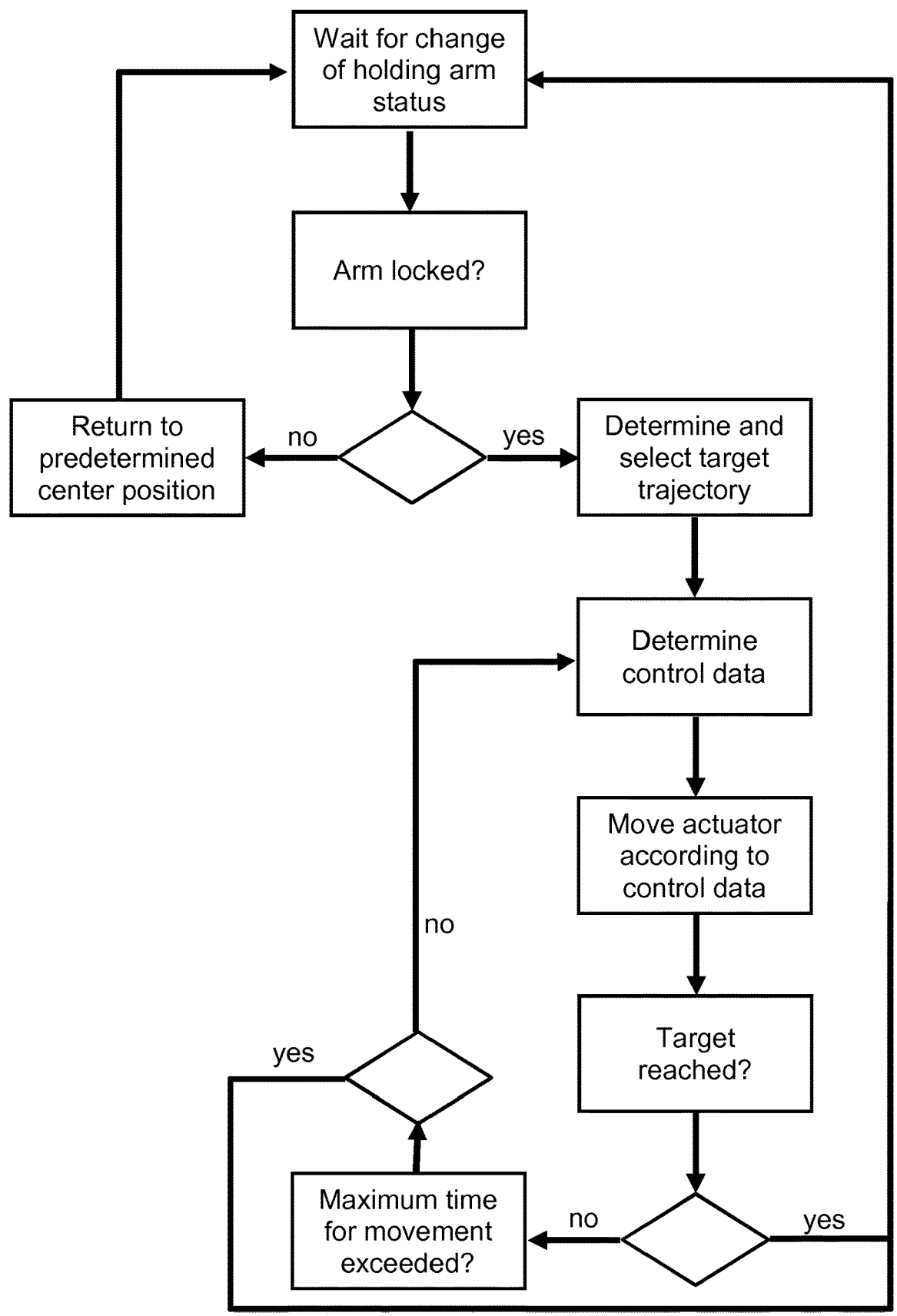
FIG. 3 is a flow diagram showing an exemplary embodiment of the disclosed method.

FIG. 3 is a flow diagram depicting an exemplary embodiment of the disclosed method. At the top of the diagram the robotic system 1 waits for a change of the status of the holding arm 2. If the robotic system 1 is in the first status (unlocked status of the holding arm 2), the actuator of the fine-adjustment unit 3 is moved to a predetermined center position. During the unlocked status a manual movement for coarse-adjustment the holding arm 2 is allowed.

If the unlocked status of the holding arm 2 is changed to the locked status (the second status of the robotic system 1) a planned trajectory (for example, a trajectory being closest to the actual position of the tool held by the fine-adjustment unit 3) is selected based on the planned position data and the actual position data. Control data for the actuator of the fine-adjustment unit 3 is determined based on the planned position data, the status change data and the actual position data. The tool held by the fine-adjustment unit 3 is moved by means of the actuator according to instructions described by the control data. If the target (for example, a target trajectory) is reached by the tool, the robotic system 1 waits for a change of the status of the holding arm 2. If the target (for example, a target trajectory) is not reached and a predetermined maximum time is not exceeded, new (for example) updated control data is determined. If the predetermined maximum time is exceeded the robotic system 1 waits for a change of the status of the holding arm 2.

The invention claimed is:

1. A computer implemented method comprising executing, on at least one processor of at least one computer, the steps of:
   acquiring image data describing an image of an anatomical structure of a patient;
   determining planned position data, based on the image data, describing at least one planned position of a tool operatively associated with a robotic system and relative to the anatomical structure of the patient;
   acquiring status change data describing a change of a status of the robotic system from at least a first status to at least a second status, wherein in the first status a manual movement of at least one part of the robotic system is allowed and in the second status the manual movement of the at least one part of the robotic system is inhibited;
   acquiring actual position data describing an actual position of an element of the robotic system relative to the anatomical structure;
   determining, based on the planned position data and the status change data and the actual position data, control data for controlling, in the second status of the robotic system, at least one actuator to move the tool;
   transmitting the control data to the at least one actuator to control the at least one actuator in at least one of the first status or the second status;
   wherein determining the control data comprises selecting the planned position of the tool out of a plurality of planned positions based on a proximity to the actual position of the element of the robotic system.

2. The method according to claim 1, wherein the robotic system comprises a holding arm and a robotic fine-adjustment unit comprising the at least one actuator, the holding arm being manually moved for a coarse-adjustment.

3. The method according to claim 2 wherein the first status is an un-locked status of the holding arm in which the manual movement of the holding arm is allowed, and the second status is a locked status of the holding arm in which the manual movement of the holding arm is inhibited.

4. The method according to claim 1, wherein the planned position is associated with a trajectory comprising an entry point and a target point of the tool relative to the anatomical structure of the patient.

5. The method according to claim 1, wherein the control data describes instructions for controlling the at least one actuator to move the tool from the actual position to the planned position.

6. The method according to claim 1, wherein the control data is associated with information describing a minimum distance between the tool and a part of the anatomical structure of the patient.

7. The method according to claim 1, wherein the control data is associated with information describing a maximum time for moving the tool in the second status of the robotic system.

8. The method according to claim 1, wherein the control data is associated with information describing an accuracy of movement of the robotic system.

9. The method according to claim 1, further comprising executing, on the at least one processor of the at least one computer:

acquiring atlas data describing an image-based model of the anatomical structure, wherein determining the planned position data is further based on the atlas data by comparing the atlas data to the image data, wherein the comparing is implemented by applying an image fusion algorithm to the image data and the atlas data.

10. The method according to claim 1, wherein the control data comprises instructions for controlling the at least one actuator to move to a predetermined position, when the status of the robotic system changes from the second status to the first status.

11. A computer implemented method comprising executing, on at least one processor of at least one computer, the steps of:
acquiring image data describing an image of an anatomical structure of a patient;
determining planned position data, based on the image data, describing at least one planned position of a tool operatively associated with a robotic system and relative to the anatomical structure of the patient;
acquiring status change data describing a change of a status of the robotic system from at least a first status to at least a second status, wherein in the first status a manual movement of at least one part of the robotic system is allowed and in the second status the manual movement of the at least one part of the robotic system is inhibited;
acquiring actual position data describing an actual position of an element of the robotic system relative to the anatomical structure;
determining, based on the planned position data and the status change data and the actual position data, control data for controlling, in the second status of the robotic system, at least one actuator to move the tool;
transmitting the control data to the at least one actuator to control the at least one actuator in at least one of the first status or the second status;
wherein the control data is associated with information describing a maximum time for moving the tool in the second status of the robotic system.

12. A computer implemented method comprising executing, on at least one processor of at least one computer, the steps of:
acquiring image data describing an image of an anatomical structure of a patient;
determining planned position data, based on the image data, describing at least one planned position of a tool operatively associated with a robotic system and relative to the anatomical structure of the patient;
acquiring status change data describing the change of a status of the robotic system from at least a first status to at least a second status, wherein in the first status a manual movement of at least one part of the robotic system is allowed and in the second status the manual movement of the at least one part of the robotic system is inhibited;
acquiring actual position data describing an actual position of an element of the robotic system relative to the anatomical structure;
determining, based on the planned position data and the status change data and the actual position data, control data for controlling, in the second status of the robotic system, at least one actuator to move the tool;
transmitting the control data to the at least one actuator to control the at least one actuator in at least one of the first status or the second status;
wherein the control data comprises instructions for controlling the at least one actuator to move to a predetermined position, when the status of the robotic system changes from the second status to the first status.

13. A non-transitory computer readable storage medium storing computing device instructions executable by a processor to perform a method comprising:
acquiring image data describing an image of an anatomical structure of a patient;
determining planned position data, based on the image data, describing at least one planned position of a tool operatively associated with a robotic system and relative to the anatomical structure of the patient;
acquiring status change data describing a change of a status of the robotic system from at least a first status to at least a second status, wherein in the first status a manual movement of at least one part of the robotic system is allowed and in the second status the manual movement of the at least one part of the robotic system is inhibited;
acquiring actual position data describing an actual position of an element of the robotic system relative to the anatomical structure;
determining, based on the planned position data and the status change data and the actual position data, control data for controlling, in the second status of the robotic system, at least one actuator to move the tool;
wherein determining the control data comprises selecting a planned position of the tool out of a plurality of planned positions based on a proximity to an actual position of the element of the robotic system.

14. A robotic system to control automated movement of a tool associated with the robotic system, the robotic system comprising:
at least one holding arm;
at least one robotic fine-adjustment unit comprising at least one actuator; and
at least one computer having at least one processor;
wherein the at least one computer is operatively associated with the at least one actuator; and
the at least one processor having associated memory with instructions which, when executed by the at least one processor, causes the at least one processor to: acquire image data describing an image of an anatomical structure of a patient;
determine planned position data, based on the image data, describing at least one planned position of a tool operatively associated with the robotic system and relative to the anatomical structure of the patient;
acquire status change data describing the change of a status of the robotic system from a first status to a second status, wherein in the first status a manual movement of at least one part of the robotic system is allowed and in the second status a manual movement of the at least one part of the robotic system is inhibited;
acquire actual position data describing the actual position of at least one of the tool or an element of the robotic system, relative to the anatomical structure; and,
determine, based on the planned position data and the status change data and the actual position data, control data for controlling, in the second status of the robotic system, at least one actuator to move the tool;
wherein determining the control data comprises selecting a planned position of the tool out of a plurality of planned positions based on a proximity to an actual position of the element of the robotic system.

15. The system of claim 14 wherein the control data is associated with information describing a minimum distance between the tool and a part of the anatomical structure of the patient.

* * * * *